US006441242B1

(12) United States Patent
Kuhn et al.

(10) Patent No.: US 6,441,242 B1
(45) Date of Patent: Aug. 27, 2002

(54) PROCESS FOR THE PREPARATION OF BENZYLACETONE

(75) Inventors: Walter Kuhn, Holzminden; Hans-Ulrich Funk, Lauenförde; Gerhard Senft, Holzminden, all of (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/948,026

(22) Filed: Sep. 5, 2001

(30) Foreign Application Priority Data

Sep. 8, 2000 (DE) .......................... 100 44 400

(51) Int. Cl.$^7$ .............................................. C07C 45/73
(52) U.S. Cl. ...................... 568/318; 585/266; 585/269
(58) Field of Search ........................ 568/318; 585/266, 585/269

(56) References Cited

U.S. PATENT DOCUMENTS

| | | | |
|---|---|---|---|
| 3,860,657 A | 1/1975 | Easter, Jr. et al. | 260/601 R |
| 4,146,581 A | 3/1979 | Nissen et al. | 260/586 |
| 4,450,300 A | 5/1984 | Fischer et al. | 568/462 |
| 6,150,564 A | 11/2000 | Bröcker et al. | 568/462 |

FOREIGN PATENT DOCUMENTS

| | | |
|---|---|---|
| EP | 0 034 804 | 9/1981 |
| PL | 153 267 | 3/1991 |

OTHER PUBLICATIONS

Database CAPLUS on STN, Acc. No. 1986:224646, Alba et al., Reduction of benzylidenacetone and acetophenone over palladium/aluminum orthophosphate and palladium/silica catalysts. Appl. Catal. 1985, 17(2), pp. 223–231 (abstract).*

Database CAPLUS on STN, Acc. No. 1984:437983, Alba et al., 'Reduction of benzylideneacetone derivatives with palladium/silicon dioxide–aluminum phosphate as catalyst and cyclohexene as hydrogen donor.' Can. J. Chem., 1984, 62(5), pp. 917–921 (abstract).*

Database CAPLUS on STN, Acc. No. 1992:530696, Esteruelas et al., 'Hydrogenation of benylideneacetone catalyzed by chlorodihydridobis(diisopropylphosphine)iridium . . . ' Inorg. Chem., 1992, 31(19), pp. 4013–4014 (abstract).*

Database CAPLUS on STN, Acc. No. 1990:98099, Spogliarich et al., 'Selective hydrogenation of benzylideneacetone catalyzed by iridium disphosphene complexes.' J. Mol. Cat., 50(1), pp. 19–29 (abstract).*

Parfümerie un Kosmetik, Apr. 1988 (date unavailable) pp. 211–212, Selektive Hydrierung von Benzylidenaceton zum Benzylaceton, Andrzej Malasiewicz, Maria Beldowicz, Iwona Szydlowska, Wladyslaw S. Brud.

Common Fragrance and Flavor Materials, K. Bauer and A. Garbe, p. 73, (month unavailable) 1985, Aromatic Compounds.

Chem. Pharm. Bull. 38(6) pp. 1720–1723, (month unavailable) 1990, Studies of Reduction with Dimethoxyborane–Transition Metal Boride Systems, Atsuko Nose and Tadahiro Kudo.

Ber. Dtsch. Chem. Ges., 56, (month unavailable) 1923, pp. 2172–2178, Julius v. Braun un Gerd Kochendorfer: Katalytische Hydrierungen unter Druck bei Gegenwart von Nickel salzen, VII.: Aldehyde.

Annales De Chimie, 9(1), (month unavailable) 1914, pp. 88–93, Hecherches Sur Les Azotites, M. Oswald.

Synthetic Communications, 28(22), pp. 4193–4200 (month unavailable) 1998, Catalytic Transfer Hydrogenation of Unsaturated Ketones and Imides Via Ammonium Frormate, P.P. Pande, G.C. Joshi and C. S. Mathela.

Synlett, Jan. 1991, pp. 27–28, Palladium–Catalyzed Conjugate Reduction of α, β–Unsaturated Carbonyl Compounds with Potassium Formate, Antonio Arcadi, Emilia Bernocchi, Sandro Cacchi, Fabio Marinelli.

React. Kinet. Catal. Lett., vol. 25, Nos. 1–2, 45–50 (month unavailable) 1984, Liquid Phase Reduction of α, β–Unsaturated Catalyst, A. Alba, M.A. Aramendia, V. Borau, C. Jimenez and J.M. Marinas.

* cited by examiner

Primary Examiner—Brian J. Davis
(74) Attorney, Agent, or Firm—Joseph C. Gil; Noland J. Cheung

(57) ABSTRACT

Benzylacetone can be prepared by hydrogenating benzylideneacetone in the presence of a palladium catalyst on activated carbon and/or a palladium catalyst on aluminum oxide.

7 Claims, No Drawings

PROCESS FOR THE PREPARATION OF BENZYLACETONE

BACKGROUND OF THE INVENTION

Benzylacetone is a valuable fragrance and flavor which occurs in the cocoa bean. Its odor is similar to the scent of jasmine and strawberry. Benzylacetone is used in fragrance compositions and aromas (Malasiewicz, Parfümerie und Kosmetik, p. 211, 4/88, K. Bauer, A. Garbe, Common Fragrance and Flavor Materials, p. 73, VCH, Weinheim, 1985).

It is known to prepare benzylacetone (1-phenyl-3-butanone) by selective hydrogenation of the double bond of benzylidene acetone. During the hydrogenation, the carbonyl group and the aromatic ring are retained.

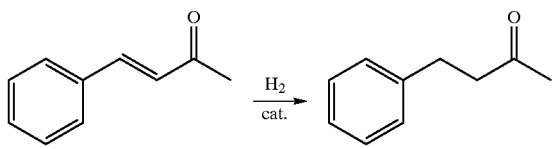

For the hydrogenation with hydrogen, use is made, for example, of nickel catalysts (Chem. Pharm. Bull., 1990, 38(6), 1720), in particular Raney nickel (Ber. Dtsch. Chem. Ges. 56,2174 (1923)).

PL 153267 describes an activated nickel catalyst on aluminum oxide, with which benzylacetone can be prepared in 82% yield from benzylideneacetone at 100–150° C.

For the preparation of benzylacetone, noble metal catalysts, such as platinum black, are also known (Ann. Chim. 9, (1), 90, (1914)).

It is also known to prepare benzylacetone using a catalyst of palladium on activated carbon in a solution of acetic acid/ammonium formate with a yield of 78% (Synth. Commun. (1998), 28(22), 4193).

It is also known to prepare benzylacetone using a catalyst of palladium acetate in dimethylformamide in the presence of potassium formate with a yield of 97% (Synlett. 1991,1, 27).

It is also known to prepare benzylacetone using a catalyst of palladium on silicon dioxide/aluminum phosphate in methanolic solution with a selectivity of 100% (React. Kinet. Catal. Lett, 25, 45–50 (1984)).

It is also known to prepare benzylacetone using a catalyst combination of palladium or platinum with the rare earths, such as lanthanum, praseodymium (DE-A 2 615 308).

In the case of industrial-scale production, the known processes for the preparation of benzylacetone from benzylidene acetone exhibit disadvantages by virtue of the toxicity of the catalyst, by virtue of the uneconomical nature because of the dilution with solvents, by virtue of yields which are too low or by virtue of catalysts which have to be prepared in a complex manner.

There is still the need to find a process which gives benzylacetone in an ecologically acceptable and economical manner.

SUMMARY OF THE INVENTION

We have found a process for the preparation of benzylacetone by hydrogenation of benzylideneacetone, which is characterized in that the hydrogenation is carried out in the presence of a palladium catalyst on activated carbon and/or a palladium catalyst on aluminum oxide.

DETAILED DESCRIPTION OF THE INVENTION

The process according to the present invention is preferably carried out without solvents.

Using the process according to the present invention, it is possible to prepare benzylacetone in high yields in an economic manner. The handling of palladium as catalyst is particularly advantageous since the catalyst does not represent a hazardous substance.

For the process according to the present invention, the palladium catalyst can be used in the dry or moist (residual moisture of water) state.

For the process according to the present invention, the proportion of palladium on the support material of activated carbon and/or aluminum oxide can be 1 to 50% by weight, preferably 5 to 10%, based on the dry catalyst.

For the process according to the present invention, the weight ratio of the catalyst used to benzylideneacetone is preferably 0.00001 to 0.01, more preferably 0.0001 to 0.001:1.

The reaction temperature for the process according to the present invention is preferably 20 to 100° C., more preferably 50–80° C.

The hydrogen pressure is preferably 1 to 20 bars, more preferably 1 to 5 bars.

The reaction time is preferably 1 to 20 hours, more preferably 6 to 15 hours.

The process according to the present invention can be carried out as follows:

A reaction vessel with gas-dispersion stirrer is charged with benzylideneacetone and e.g. palladium on activated carbon 5% by weight. Hydrogenation is carried out at a hydrogen pressure of e.g. 1 bar. The crude product is filtered and distilled.

It is surprising that the hydrogenation can be carried out in high yield and selectively in the presence of a palladium catalyst on activated carbon and/or a palladium catalyst on aluminum oxide.

EXAMPLES

Example 1

A 5 l stirred autoclave with gas-dispersion stirrer was charged with 1493 g of benzylideneacetone (GC purity 99.3%) and 1.3 g of palladium on activated carbon 5% with 40% water content. Hydrogenation was carried out for 17 hours at 55° C. The hydrogen pressure was 2 bar. Following filtration of the crude product, the gas chromatographic analysis of the reaction product gave the following composition: 98.2% of benzylacetone, 1.1% of phenylbutanol.

Distillation of the crude product at 82 to 85° C. and a vacuum of 2 mbar proceeded without residue.

Example 2

A 5 l stirred autoclave with gas-dispersion stirrer was charged with 1500 g of benzylideneacetone (GC purity 99.3%) and 0.8 g of palladium on aluminum oxide 5% dry. Hydrogenation was carried out for 6 hours at 75° C. The hydrogen pressure was 5 bar. Following filtration of the crude product, the gas chromatographic analysis of the reaction product gave the following composition: 98.7% of benzylacetone, 0.7% of phenylbutanol.

Distillation of the crude product at 82 to 85° C. and a vacuum of 2 mbar proceeded without residue.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of benzylacetone comprising the step of hydrogenating benzylideneacetone in the presence of a palladium catalyst on activated carbon and/or a palladium catalyst on aluminum oxide.

2. A process according to claim 1, wherein the palladium catalyst is used in the dry or moist state for the hydrogenation.

3. A process according to claim 1, wherein the proportion of palladium on the support material activated carbon and/or aluminum oxide is 1 to 50% by weight, based on dry catalyst.

4. A process according to claim 1, wherein the reaction is carried out without solvents.

5. A process according to claim 1, wherein the weight ratio of the catalyst used to benzylideneacetone is 0.00001 to 0.01:1.

6. A process according to claim 1, wherein the reaction temperature is 20 to 100° C.

7. A process according to claim 1, wherein the hydrogen pressure is 1 to 20 bar.

* * * * *